United States Patent [19]

Szabo et al.

[11] Patent Number: 5,234,908
[45] Date of Patent: Aug. 10, 1993

[54] METHOD OF TREATING GASTROINTESTINAL ULCERS WITH PLATELET DERIVED GROWTH FACTOR

[75] Inventors: Sandor Szabo, Brookline; Marc F. Charette, Needham, both of Mass.

[73] Assignees: Creative BioMolecules, Inc., Hopkinton; Brigham & Womens Hospital, Boston, both of Mass.

[21] Appl. No.: 866,822

[22] Filed: Apr. 10, 1992

Related U.S. Application Data

[63] Continuation-in-part of Ser. No. 685,085, Apr. 12, 1991, abandoned.

[51] Int. Cl.[5] ............................................. A61K 37/36
[52] U.S. Cl. ................................... 514/12; 514/8; 514/21
[58] Field of Search ................................ 514/21, 12

[56] References Cited

U.S. PATENT DOCUMENTS 4,350,687 9/1982 Lipton et al.
4,479,896 10/1984 Antoniades.

Primary Examiner—Howard E. Schain
Attorney, Agent, or Firm—Testa, Hurwitz & Thibeault

[57] ABSTRACT

Disclosed is a method for treating ulcers of the gastrointestinal tract in a mammal which includes administering to the mammal a therapeutically effective amount of Platelet-Derived Growth Factor (PDGF) to the gastrointestinal tract of the mammal.

13 Claims, No Drawings

METHOD OF TREATING GASTROINTESTINAL ULCERS WITH PLATELET DERIVED GROWTH FACTOR

This application is a continuation-in-part of U.S. Ser. No. 685,085, filed Apr. 12, 1991, now abandoned.

The invention relates in general to the treatment of gastrointestinal (GI) disorders.

BACKGROUND OF THE INVENTION

Peptic ulcers include gastric ulcers, which occur as lesions in the wall of the stomach, and duodenal ulcers, which are deep lesions that occur in the wall of the duodenum, i.e., the upper portion of the small intestine. The body's main defense against the corrosive effects of potent gastric digestive juices is the mucous bicarbonate layer that lines the inside of the duodenum and stomach. Duodenal ulcers result from an imbalance in factors that maintain the natural mucous bicarbonate layer, thus leading to destruction of the epithelium and underlying connective tissues. Although current antiulcer therapeutics, including antisecretory products such as cimetidine and ranitidine, appear to be effective in healing duodenal ulcers, it is generally believed that they are effective because they reduce normal gastric acid secretion. While the reduction in acidity aids in the closure of the ulcer, it also interferes with normal digestion. Studies have shown that 40-60% of ulcers healed with current therapies recur within one year of therapy. The high rate of ulcer recurrence is thought to be at least partially attributable to the reduced number of mucus-producing cells in the scar tissue which is left at the site of the healed ulcer. This area is thus thought to be more vulnerable to rupture when the gastrointestinal acidity returns to normal.

Ulcerative colitis is an inflammatory bowel disease of the mucosal lining of the colon and rectum for which there is little effective treatment. It is a chronic debilitating disorder with high morbidity and can lead to colorectal cancer. The disease is for the most part confined to the mucosal and submucosal layers of the colonic wall, where severe inflammation of the colorectal mucosa, crypt abscesses and multiple ulcers occur. It is characterized by bloody stools, diarrhea, fever, and liver function abnormalities. More than 50% of all patients with chronic ulcerative colitis have surgery within the first two years of their illness to remove the affected tissues.

Ulcerative mucositis is a serious and dose-limiting toxic side effects of many forms of cancer chemotherapy. The lesions which occur as a consequence of this condition cause severe pain and loss of function in affected patients. The disruption in the oral mucosa results in a systemic portal of entry for the numerous microorganisms found in the mouth. Consequently, the oral cavity is the most frequently identifiable source of sepsis in the granulocytopenic cancer patient. Current therapy for mucositis is limited to either local or systemic palliation or topical antibacterial therapy.

PCT Application No. PCT/US89/03467 discloses the use of an acid-resistant fibroblast growth factor to treat GI ulcers.

SUMMARY OF THE INVENTION

The invention is based on the discovery that platelet-derived growth factor (PDGF) is a potent stimulator of growth of granulation tissue, which lies beneath the epithelial layer lining the entire gastrointestinal tract. The invention features a method of treating an ulcer present within the gastrointestinal tract of a mammal which includes administering a therapeutically effective amount of PDGF or a pharmaceutically acceptable form thereof into the gastrointestinal tract of the mammal. As used herein, the gastrointestinal tract extends from the mouth to the rectum, inclusive.

In preferred embodiments of the invention, the mammal is a human and ulcers treatable according to the invention include those found in the ileum which cause regional ileitis, those found in the colon which cause ulcerative colitis, Crohn's disease, proctitis and other forms of inflammatory bowel disease (IBD), those found in the mouth, particularly oral mucositis caused by chemotherapy or radiation therapy, and peptic ulcers such as gastric ulcers found in the stomach, or those ulcers found in the duodenum or esophagus. Preferably, PDGF is administered orally or rectally according to the invention.

As used herein, "PDGF" refers to naturally occurring PDGF, PDGF obtained by recombinant DNA techniques using either eucaryotic or bacterial host cells, as well as biologically active mutants of PDGF, biologically active fragments of PDGF and biologically active mutants of biologically active fragments of PDGF. A biologically active mutant PDGF or fragment of PDGF will retain the biologically active region of PDGF, but may differ in the amino acid sequence of the native polypeptides; i.e., a PDGF fragment may lack amino acid sequences that are not necessary for the biological activity of the protein, and a PDGF mutant may lack amino acids that are not essential to biological activity or may contain additional or may substitute amino acids whose presence do not affect the biological activity of the protein.

As used herein, "ulcer" refers to an open lesion or break of the integrity of the epithelial lining of the gastrointestinal tract, resulting in erosion of the underlying granulation tissue.

Other features and advantages of the invention will be apparent from the following description of the preferred embodiments, and from the claims.

DETAILED DESCRIPTION OF THE INVENTION

PDGF is a peptide hormone produced by blood platelets which influences the regulation of a broad array of biological systems including wound repair, arteriosclerosis, neoplasia, embryogenesis and bone marrow fibrosis. In wound repair, PDGF elicits both chemotactic and mitogenic responses in fibroblasts, smooth muscle, and glial cells. Injury to endothelial linings is believed to cause platelets to adhere to exposed connective tissue at the wound site, and thereby to release PDGF. The released PDGF is thought to chemotactically recruit fibroblasts, monocytes, glia and smooth muscle to migrate to the site of the wound. PDGF is also believed to stimulate DNA synthesis in these cells, thereby increasing their proliferation rate.

Native PDGF is a dimeric molecule composed of two polypeptid chains, one or more of which may be glycosylated. The two chains (referred to as A or alpha and B or beta) are homologous but not identical. They have molecular weights of approximately 17,000-18,000 daltons and approximately 13,000-14,000 daltons respectively. In vivo, the A and B chains are synthesized from larger precursors which are subsequently processed at the amino and carboxyl termini. The mature human A chain is composed of 110 or 125 amino acids and various N-linked sugar side chains, the length and amino acid sequence being dependent on the tissue source. The fully processed human B chain is encoded by the C-sis gene and it contains 112 amino acids. Biologically active PDGF can also exist as an AA or BB dimer having a molecular weight of about 35,000 daltons or about 32,000 daltons, respectively.

The invention provides a method for the treatment of ulcerative diseases within the GI tract of a mammal, especially a human. The GI tract, from mouth to rectum, contains a layer of epithelium covering granulation tissue. Thus, the entire GI tract, the mouth, esophagous, stomach, upper and lower intestines, and colon, contain these similar cell types. Therefore, treatment of an ulcer, e.g., of the ileum, by administration of PDGF according to the invention will also be applicable to treatment of ulcers of other regions of the GI tract, e.g., the mouth. Described below are experiments in which an ulcer of the duodenum was treated with PDGF according to the invention, and healed faster than an untreated ulcer and experiments in which PDGF may be tested for the treatment of oral mucositis and ulcerative colitis. PDGF treatment according to the invention is applicable to an ulcer in any region of the GI tract. The method of the invention, in its simplest form, includes administering to the GI tract of a mammal a therapeutically effective amount of PDGF or a pharmaceutically acceptable derivative or salt thereof via parenteral, but more preferably oral or rectal means.

PDGF can be prepared from human platelets, produced via recombinant DNA techniques, and is also commercially available. The preparation of PDGF from human platelets is described in the literature. See, for example, Heidin et al., (1979) Proc. Natl. Acad. Sci. U.S.A.76: 3722-3726; Antoniades et al., (1979) Proc. Natl. Acad. Sci. U.S.A.76: 1809-1813), Antoniades et al., U.S. Pat. No. 4,479,896, and Lipton et al., U.S. Pat. No. 4,350,687, all of which are hereby incorporated by reference. In addition, PDGF can be produced recombinantly using either transformed eucaryotic cells such as yeast, EP Publication No. 0177957, or using transformed procaryotic cells such as E.coli (Charette et al. U.S. patent application Ser. No. 07/155,066, filed Feb. 11, 1988, assigned to the same assignee and hereby incorporated by reference). PDGF is also commercially available from the Amgen Corporation (Thousand Oaks, CA), PDGF, Inc. (Boston, Mass.), Collaborative Research, Inc. (Waltham, Mass.) and Creative BioMolecules, Inc. (Hopkinton, Mass.). Preparation of PDGF for administration is accomplished by conventional techniques. For example, liquid preparation, tablets or capsules may be prepared by employing additives such as pharmaceutically acceptable carriers (e.g., lactose, corn starch, light silicic anhydride, microcrystalline cellulose, sucrose), binders (e.g., alpha-form starch, methylcellulose, carboxymethylcellulose, hydroxypropylcellulose, hydroxypropylmethylcellulose, polyvinylpyrrolidone), disintegrating agents (e.g., carboxymethylcellulose calcium, starch, low substituted hydroxypropylcellulose), surfactants e.g., Tween 80 Kao-Atlas), Pluronic F68 (Asahi Denka, Japan); polyoxyethylene-polyoxypropylene copolymer)], antioxidants (e.g., L-cysteine, sodium sulfite, sodium ascorbate), lubricants (e.g., magnesium stearate, talc), and the like. Rectal preparations are also prepared by conventional techniques, for example by employing an oleaginous base such as a higher fatty acid glyceride [e.g., cacao butter, Witepsols (a semisynthetic base) Dynamite Nobel, Federal Republic of Germany], a medium fatty acid glyceride [e.g., Miglyols (Dynamite Nobel)] or a vegetable oil (e.g., sesame oil, soybean oil, corn oil, cottonseed oil, olive oil).

When the composition is formulated into an injectable aqueous solution, the solution is prepared by conventional methods using a solvent such as an aqueous solvent (e.g., distilled water, physiological saline, Ringer's solution), or oily solvent (e.g., sesame oil, olive oil). If desired, one or more additives may be employed. Such additives include a dissolution aid (e.g., sodium salicylate, sodium acetate), buffer (e.g., sodium citrate, glycerine), isotonizing agent (e.g., human serum albumin, polyethylene glycol), preservatives (e.g., benzyl alcohol, phenol) or analgesic (e.g., benzalkonium chloride, procaine hydrochloride).

When the composition is formulated into a preparation for injection, the preparation can be produced by routine methods using, for example, a diluent (e.g., distilled water, physiological saline, glucose), excipient (e.g., carboxymethylcellulose, sodium arginate), preservative (benzyl alcohol, benzalkonium chloride, phenol), or analgesic (e.g., glucose, calcium gluconate, procaine hydrochloride).

For certain diseases of the lower GI tract, such as peptic ulcers and ulcerative colitis and other forms of inflammatory bowel disease, it is preferred that the PDGF composition be coated with an enteric copolymer such as hydroxypropylmethylcellulose phthalate, cellulose acetate phthalate or methacrylic acid copolymer to further protect the PDGF from acid and digestive enzymes such as pepsin. This coated composition thus passes into the area of GI tract where its therapeutic value is optimized.

The invention also provides for the administration of pharmaceutical compositions comprising PDGF or its salt, and one or more agents which stabilize, potentiate, or otherwise affect the therapeutic efficacy of PDGF. Such agents include: (i) stabilizing agents such as glycosaminoglycan, which include heparin, glucan sulfate such as dextran sulfate, sulfated cyclodextrins such as beta-cyclodextrin tetradecasulfate and B- 1, 3-glucan sulfate; (ii) antisecretory agents such as H2-receptor antagonists (e.g., cimetidine, ranitidine, famotidine, roxatidine acetate), muscarine receptor antagonists (e.g., pirenzepine), proton pump (ATPase) inhibitors (e.g., omerrazone); (iii) cytoprotective agents such as colloidal bismuth salts (e.g., De-Nol), sucralfate and prostaglandin derivatives; and (iv) antacids such as aluminum hydroxide gel, magnesium hydroxide and sodium bicarbonate. Such agents may be administered either separately or as a components of the composition.

The relative amount of stabilizing/potentiating agents and PDGF may vary depending on a number of factors, including the agent used, the patient's condition, and the mode of administration. In general, the weight ratio of stabilizer to PDGF is approximately 0.1 to 100, most preferably 0.2 to 20, preferably from approximately about 0.5 to 4.

Stabilizing agents which may be used in accordance with the present invention include glycosaminoglycans such as heparin, fragments of heparin, glucan sulfates such as dextran sulfate, cyclodextrin sulfate and $\beta$-1,3-glucan sulfate. The glucan sulfate employable in the present invention may also be in the form of a salt. As the salt, any pharmaceutically acceptable cation may be employed, e.g., sodium, potassium, ammonium, trimethyl ammonium, and the like.

The preferred antisecretory agents are ranitidine and cimetidine. The amount of antisecretory agent used will vary in accordance with the above-described factors. For example, when used to treat peptic ulcers, one preferred composition includes from approximately 10 to 300 μg PDGF, preferably 100 μg PDGF, and from approximately 20 to 600 mg of antisecretory agent, preferably 200 mg of antisecretory agent.

The preferred antacids include aluminum hydroxide gel, sodium bicarbonate and magnesium hydroxide. The antacid may be taken in conjunction with PDGF or may be incorporated as one component of the PDGF composition itself. The amount of antacid should generally be from 0.5 to 5.0 gm per treatment.

The amount of cytoprotective agent used will depend on a number of factors, including the agent used. Generally, between 2.5 to 5 μg of prostaglandin derivative per adult human, and 0.5 μg of sucralfate per adult human is used.

A representative example of a PDGF preparation is PDGF in combination with the stabilizer glucan sulfate. When the PDGF protein component of the present invention is brought into contact with glucan sulfate in an aqueous medium, it is preferably conducted in the presence of di- or tri-basic carboxylic acid to give an even more stabilized PDGF. Examples of di-basic carboxylic acid include tartaric acid, maleic acid, malic acid and fumaric acid. Examples of tri-basic carboxylic include citric acid and iso-citric. The above-mentioned carboxylic acids may also be in the form of a salt. It may also be possible that native carboxylic acid be added to an aqueous medium, to which is added an adequate amount of an alkali or an acid to adjust the pH desirably.

Bringing the PDGF protein component into contact with glucan sulfate and further with carboxylic acid in an aqueous medium is accomplished by mixing these materials in an aqueous medium. The aqueous medium is preferably comprised of distilled water, physiological saline, glucose solution, buffers such as phosphate buffer and tris-hydroxymethylaminomethane-HCl buffer. An aqueous solution of PDGF protein component, an aqueous solution of glucan sulfate and an aqueous solution of carboxylic acid may be mixed, or a mixture of these materials in solid form may be dissolved in water. The mixing of these materials is conducted at temperatures ranging from 3° to 10° C., more preferably from about 5° to 9° C. The time required for mixing is usually in the range of from about 1 to 30 minutes. The resulting composition may be lyophilized, during which procedure a complex may be formed and recovered. For separating and recovering the resultant stabilized PDGF composition a gel-filtration method using Sephadex gel, or an ion-exchange chromatography using DEAE- or CM- Toyopearl may be used. Alternatively, the stabilized PDGF composition can be used as it is without separation or recovery.

Dosage and Mode of Administration

The preferred mode of administration of GI ulcers according to the invention is orally, e.g., by tablet, capsule, lozenge or chewable gum, or rectally by suppository or enema. Other routes of administration for disease of the GI tract include parenterally, e.g., intravenously or subcutaneously.

The dosage of PDGF required to treat GI ulcers in human adult patients is generally from about 0.1 μg to 30 mg per day, preferably from about 0.1 μg to 10 mg, more preferably from about 1.0 μg to 3 mg per day, and most preferably from about 10 μg to 300 μg per day. For oral administration, 10 μg to 150 μg of PDGF or its salt may be formulated as a tablet or a capsule together with a pharmaceutically acceptable carrier, diluent or other suitable vehicle. Such a formulation is beneficially administered one to four times daily to bring the dosage within the preferred range.

The invention will be further understood with reference to the following examples.

PDGF Treatment of Induced Duodenal Ulcer

In the following experiments, ulcers were induced in rats and then subsequently treated with PDGF.

Sprague-Dawley female rats (150–200 grams) received the duodenal ulcerogen cysteamine-HCl at a dose of 25 milligrams (mg) per 100 grams (gm) of body weight orally by intragastric gavage 3 times on the same day. Additionally, cortisol was administered subcutaneously to each rat at a single dose of 5 mg of cortisol to 100 gm of body weight to decrease the mortality resulting from the administration of the cysteamine-HCl.

Three days after administration of the cysteamine-HCl, rats having penetrating and perforating duodenal ulcers were determined by laparotomy and were randomized into control and PDGF-treated groups.

Group 1 included nine rats with ulcers. All nine rats in group 1 received no PDGF and were treated only with saline. The rats were treated with the saline vehicle by gavage twice daily until autopsy on day 21, when the ulcers were measured and histologic sections taken.

Group 2 included five rats, each of which received 100 ng of PDGF per 100 gm of body weight by gavage twice daily until autopsy on day 21, when ulcers were measured and histologic sections taken.

Group 3 included five rats, each of which received 500 ng of PDGF per 100 gm of body weight by gavage twice daily until autopsy on day 21, when ulcers were measured and histologic sections taken.

Ulcer measurements with and without PDGF treatment and in the control group are presented in Table 1.

TABLE 1

| Group 1 | |
| --- | --- |
| Ulcer incidence = | 100% |
| Ulcer crater = | 16.9 ± 6.8 mm$^2$ |
| Group 2 | |
| Ulcer incidence = | 60% |
| Ulcer crater = | 2.5 ± 1.1 mm$^2$ ($p = 0.051$) |
| Group 3 | |
| Ulcer incidence = | 29% |
| Ulcer crater = | 2.05 ± 1.4 mm$^2$ ($p = 0.048$) |

Histology of duodenal sections from PDGF-treated animals revealed healed ulcers with prominent and dense granulation tissue and partial or complete re-epitheliazation.

Thus, the results demonstrate that oral administration of PDGF can significantly accelerate the healing of ulcers of the GI tract.

Gastric acid and Pepsin Secretion of PDGF Treated Rats

In the following experiments, secretory levels of gastric acid and pepsin were measured in PDGF-treated and control rats.

Group 1 included eight to ten rats which were fasted for 24 hours and given saline vehicle and 30 mg of latex under ether anesthesia. The stomachs of the rats were constricted with a pyloric ligature for one hour.

Group 2 included eight to ten rats which were fasted for 24 hours and given 500 ng of PDGF per 100 gm of body weight by syringe orally. The stomachs of the rats were then constricted with a pyloric ligature for one hour.

Gastric juice was then collected from each rat in groups 1 and 2, centrifuged and aliquots processed for acid titration to calculate gastric acid output and pepsin determination. Gastric acid was measured by the acidity of the gastric juices and pepsin levels were determined according to standard protease assays well-known in the art. Since pepsin is the most abundant protease in the stomach, the total protease level is a good measurement of the pepsin level. The gastric juice aliquots were spectrophotometrically analyzed using albumin as a substrate. (Szabo, S. et al., Res. Comm. Chem. Pathol. Pharmacol., 1977, 16, 311-323, hereby incorporated by reference).

Group 1, the control rats which received saline rather than PDGF, had normal levels of gastric pepsin. In Group 2, which included the PDGF-treated rats, no decrease in gastric juice volume acid or pepsin outputs were observed. Thus, PDGF treatment of ulcers of the GI tract do not affect the normal levels of gastric acid or pepsin in the GI tract.

PDGF Treatment of Oral Mucositis

Oral mucositis involves ulcerations of the mouth as a consequence of, e.g., radiation therapy or chemotherapy. The course of ulcerative mucositis may be divided into a destructive phase and a healing phase. Since the cells of the basal layer of the oral epithelium divide at a rapid rate, they are susceptible to the antimitogenic and toxic effects of chemotherapy. As a result, atrophic changes occur which are then followed by ulceration. This constitutes the destructive phase. Following ulcer formation, the lesions slowly resolve during the healing phase PDGF is a known stimulator of epithelial cell proliferation. Its efficacy in reducing healing time of mucositis may be evaluated by experimental procedures known to those skilled in the art, one example of which follows.

The effect of PDGF on male golden syrian hamsters, 6-8 weeks old (Charles River Laboratories, Wilmington, Mass.) will be tested. The animal test groups will include a placebo control group (1), a PDGF low dose group (2) and a PDGF high dose group (3). Each group will contain 12 animals.

On day 0, all five groups of animals will begin the mucositis-induction procedure. Five fluorouracil (60 mg/kg) will be injected intraperitoneally on days 0 and 5. On day 2, the right buccal pouch mucosa will be superficially irritated with a calibrated 18 gauge needle. Severe ulcerative mucositis should be induced in at least 80% of the animals by day 7.

On day 5, hamsters in groups 2 and 3 will receive twice daily applications of PDGF (about 100-500 ng/100 gm). Animals will continue to receive PDGF until day 18. Animals in Group 1 will receive placebo from day 0 to day 18.

The vehicle control or PDGF material will be administered following gentle drying of the cheek pouch mucosa, followed by even application over the mucosal surface of the vehicle or PDGF material. A hydroxypropylcellulose based coating will be used to maintain contact of the PDGF with the mucosa. This coating will provide at least 4 hours of contact time.

On day 9, two animals in each group will be sacrificed for histological studies. The right buccal pouch mucosa and underlying connective tissue will be dissected and fixed in 10% formalin. The specimens will be mounted in paraffin and prepared for histologic examination. Sections will be stained with hematoxylin and eosin and will be examined blindly by an oral pathologist with expertise in hamster histology. The extent of atrophy, cellular infiltration, connective tissue breakdown, degree of ulceration and epithelialization will be assessed.

The oral ulcers will then be observed for evidence of accelerated healing relative to the control group. The remaining hamsters will be examined and weighed daily, and the right buccal cheek pouch will be averted and photographed.

Cheek pouch photographs will be numbered, randomized, and scored blind by 3 observers against a standard mucositis panel. The mean mucositis score for each group will be determined for each experimental day. Differences between groups will be determined using the Students' 't' test. In addition, data will be evaluated between groups by comparing the numbers of animals with severe mucositis using Chi Square statistical analysis. The significance of differences in mean daily weights will also be determined. It is expected that such treatment with PDGF will reduce injury by healing of ulcerative tissue of the oral cavity.

PDGF Treatment of Ulcerative colitis

Ulcerative colitis involves ulcers of the colon. The effect of PDGF treatment on colon ulcers may be evaluated by experimental procedures known to those skilled in the art, one example of which follows.

Guinea pigs, 500-550 gms, (Charles River laboratories) will be housed in individual cages and temperature-controlled rooms, and fed with Guinea Pig Chow (Purina Co., St. Louis, Mo.) and water ad libitum. After 48 hours of resting, the animals will be divided into 3 experimental groups.

All three groups will be fed distilled water containing degraded carrageenin (a polysaccharide derived from red seaweeds, Glaxo Laboratories, Paris, France). Carrageenin is a known inducer of ulcerative colitis in guinea pigs. In the control group (1), 20 guinea pigs will receive water containing 0% degraded carrageenin. In groups 2 and 3, 20 guinea pigs in each group will receive water containing 1% and 5% degraded carrageenin, respectively. This will continue for 30 days. During this period of time, the animals will be observed and weighed daily.

The development of colitis will be determined using several criteria: 1) presence of loose and/or bloody feces by visual inspection, 2) detection of occult blood in the feces using Coloscreen III with hemocult developer (Helena Labs, Bumont, Tex.), and 3) weight loss.

At day 25, each animal will be anesthetized with Ketamine (3-5 mg/kg) administered intramuscularly and a 3 mm colorectal mucosa biopsy will be taken using a small nasal scope. All of the specimens will be fixed in 15% formaldehyde and examined histologically using hematoxylin and eosin. The pathologic diagnosis of ulcerative colitis will be established by the presence of crypt abscesses, lymphocytic infiltration, capillary congestion of the lamina propria and ulceration of the colon mucosa (Onderdonk, Digestive Disease Science 30:40(s), 1985, hereby incorporated by reference). The severity of ulcerative colitis will be graded on a scale of 0 to 3 and expressed as the pathological index according to the standard scoring system (Onderdonk et al., Amer. J. Clin. Nutrition 32:258, 1979, Okayasu et al., Gastroenterology 98:694, 1990, both of which are hereby incorporated by reference).

At day 30, 25% of the guinea pigs in which ulcerative colitis was demonstrated histologically will be treated with PDGF and the remaining 25% will receive distilled water as a control. PDGF will be administered at a low dose of 100 ng/100 gm in one-half of the guinea pigs, and the remaining half will receive a high dose (500 ng/100 gm) of PDGF, administered orally through a 3 mm bulbed needle, twice per day for a period of 10 days (days 28-37).

During treatment, the animals will be evaluated clinically and improvements in body weight, stool consistency and reduction or absence of blood in stools will be recorded. At day 37, all animals will be sacrificed with an overdose of pentobarbital (>200 mg/kg) and the entire colon will be removed to study the effectiveness of PDGF treatment in healing carrageenin-induced colon ulcers.

Statistical analysis will be performed using SAS repeated measures analysis of variance (ANOVA), blocking in animals with post-hoc pairwise comparison by the Newman-Keuls test. A significance level of $p<0.05$ will be accepted as significant. Data organization and analysis will be assisted by the Clinfo Data Management and Analysis System (Brigham and Women's Hospital, Boston, Mass.). It is expected that treatment with PDGF will induce significant healing of ulcerative tissue of the colon.

Other Embodiments

Other embodiments of the invention are within the following claims.

We claim:

1. A method of treating an ulcer present within the gastrointestinal tract of a mammal comprising administering non-parenterally a therapeutically effective amount of platelet-derived growth factor into the gastrointestinal tract of the mammal.

2. The method of claim 1 wherein the ulcer is present the ileum.

3. The method of claim 1 wherein the ulcer is present in the colon.

4. The method of claim 1, wherein the ulcer is present in the mouth.

5. The method of claim 1, wherein the ulcer comprises a peptic ulcer.

6. The method of claim 5, wherein said peptic ulcer is present within the duodenum.

7. The method of claim 5, wherein said peptic ulcer is present in the stomach.

8. The method of claim 5, wherein said peptic ulcer is present in the esophagus.

9. The method of any one of claims 1-8 wherein said mammal is a human.

10. The method of any one of claims 1-8 wherein PDGF is administered orally.

11. The method of claim 9 wherein PDGF is administered orally.

12. The method of any one of claims 1-3 and 5-8 wherein PDGF is administered rectally.

13. The method of claim 9 wherein PDGF is administered rectally.

* * * * *